(12) United States Patent
Bindl et al.

(10) Patent No.: US 9,126,896 B2
(45) Date of Patent: Sep. 8, 2015

(54) SYNTHESIS OF DIAMIDO GELLANTS BY USING DANE SALTS OF AMINO ACIDS

(71) Applicant: EVONIK INDUSTRIES AG, Essen (DE)

(72) Inventors: Martin Bindl, Ludwigshafen (DE); Roland Herrmann, Maintal (DE); Gunter Knaup, Bruchkobel (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/386,540

(22) PCT Filed: May 13, 2013

(86) PCT No.: PCT/EP2013/059757
§ 371 (c)(1),
(2) Date: Sep. 19, 2014

(87) PCT Pub. No.: WO2013/178450
PCT Pub. Date: Dec. 5, 2013

(65) Prior Publication Data
US 2015/0073172 A1 Mar. 12, 2015

Related U.S. Application Data

(60) Provisional application No. 61/654,741, filed on Jun. 1, 2012.

(51) Int. Cl.
*C07C 231/02* (2006.01)
*C11D 3/32* (2006.01)
*C11D 7/32* (2006.01)
*C11D 17/00* (2006.01)
*C07C 227/18* (2006.01)

(52) U.S. Cl.
CPC ............ *C07C 231/02* (2013.01); *C07C 227/18* (2013.01); *C11D 3/32* (2013.01); *C11D 7/3263* (2013.01); *C11D 17/003* (2013.01); *C07C 2101/14* (2013.01)

(58) Field of Classification Search
CPC ...... C07C 231/02; C07C 227/18; C07C 2101/14; C11D 7/3263; C11D 17/003; C11D 3/32
USPC ...................................... 564/136; 560/41, 171
See application file for complete search history.

(56) References Cited

U.S. PATENT DOCUMENTS

2006/0149096 A1* 7/2006 Tyagi et al. .................... 562/442

OTHER PUBLICATIONS

Wagler et al., "Synthesis of a chiral dioxo-cyclam derived from L-phenylalanine and its application to olefin oxidation chemistry", Tetrahedron Letters, vol. 29, No. 40, pp. 5091-5094, 1988.

* cited by examiner

*Primary Examiner* — Shailendra Kumar
(74) *Attorney, Agent, or Firm* — Reed Smith LLP; Eric J. Evain; Maryellen Feehery Hank

(57) ABSTRACT

The invention relates to a method for the synthesis of a compound according to formula I comprising the following steps: a) reacting a Dane salt according to formula II and a Dane salt according to formula III with a coupling reagent; b) adding a diamine according to formula IV to the reaction mixture; and c) adding an acid to the reaction mixture to adjust the pH value of the reaction to <7; wherein L represents a $C_2$-$C_{20}$ alkyl group, a $C_6$-$C_{20}$ aryl group, or a $C_7$-$C_{20}$ alkylaryl group; $R^1$ and $R^2$ can be identical or different and represent a hydrogen atom, a $C_1$-$C_4$ alkyl group, a $C_1$-$C_4$ hydroxyalkyl group, a $C_1$-$C_4$ thioether group, a $C_6$-$C_{20}$ aryl group, a $C_7$-$C_{20}$ alkylaryl group, a $C_7$-$C_{20}$ alkylhydroxyaryl group, a $C_4$-$C_{20}$ alkylheteroaryl group with 1 to 4 heteroatoms; or a $C_1$-$C_4$ alkylcarboxylic moiety, which may be an acid, an amide, or which may be esterified with a $C_1$-$C_6$ alkyl group or a $C_7$-$C_{20}$ alkylaryl group; $R^3$ represents a $C_1$-$C_4$ alkyl group; $R^4$ represents a hydrogen atom, or a $C_1$-$C_4$ alkyl group; $R^5$ represents a $C_1$-$C_4$ alkyl group; and X represents an alkali metal.

20 Claims, No Drawings

SYNTHESIS OF DIAMIDO GELLANTS BY USING DANE SALTS OF AMINO ACIDS

CROSS REFERENCE TO RELATED APPLICATIONS

This application is a National Phase filing under 35 U.S.C. §371 of PCT/EP2013/059757 filed on May 13, 2013; and this application claims the benefit of U.S. Provisional Application No. 61/654,741 filed on Jun. 1, 2012; the entire contents of each application is hereby incorporated by reference.

The present invention relates to a method for the synthesis of diamido gellants from diamines and the Dane salts of amino acids.

Diamido compounds of the general formula

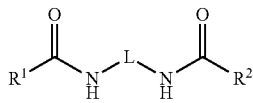

wherein $R^1$ and $R^2$ are amino-functional end-groups and L is a linking moiety of molecular weight from 14 to 500 g/mol are known in the art to serve as gellants to thicken liquid compositions. Such gellants have, for example, been described in WO 2011/112912 A1 and WO 2011/112887 A1.

Gellants are used to provide structure and a pleasant texture to liquid consumer products such as, for example, liquid detergent compositions. Furthermore, gellants can stabilize other components within the product such as, for example, enzymes and bleaches. However, gellants need to be selected carefully to prevent incompatibilities between the gellant and other components of the composition and unwanted side effects such as clouding of the liquid composition.

Diamido gellants offer the significant advantage over other gellants of being compatible with a broad range of consumer products and not affecting product clarity.

A synthesis of diamido gellants is described in WO 2011/112887 A1. In this synthesis, N-benzyloxycarbonyl-L-valine is coupled to diaminopropane using N,N'-Dicyclohexylcarbodiimide as coupling reagent. The currently known synthesis of diamido gellants therefore requires the use of N-benzyloxycarbonyl or N-(tert-butyloxycarbonyl) protected amino acids. However, such a synthesis method is expensive, mainly due to the cost of the protected amino acids, and requires additional steps to remove the protecting groups.

Hence, there is the need for a cheaper and faster strategy for the synthesis of diamido gellants.

To this end, the present invention provides a method for the synthesis of a compound according to formula I

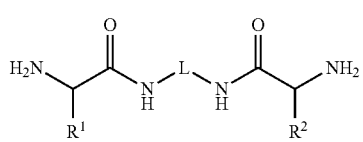

comprising the following steps:
a) reacting a Dane salt according to formula II

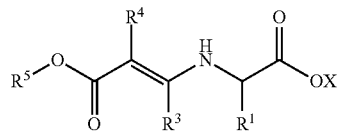

and a Dane salt according to formula III

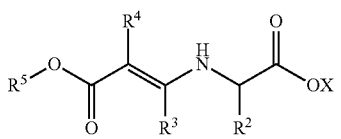

with a coupling reagent;
b) adding a diamine according to formula IV

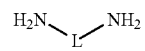

to the reaction mixture; and
c) adding an acid to the reaction mixture to adjust the pH value of the reaction to <7;
wherein
L represents a $C_2$-$C_{20}$ alkyl group, a $C_6$-$C_{20}$ aryl group, or a $C_7$-$C_{20}$ alkylaryl group;
$R^1$ and $R^2$ can be identical or different and represent a hydrogen atom, a $C_1$-$C_4$ alkyl group, a $C_1$-$C_4$ hydroxyalkyl group, a $C_1$-$C_4$ thioether group, a $C_6$-$C_{20}$ aryl group, a $C_7$-$C_{20}$ alkylaryl group, a $C_7$-$C_{20}$ alkylhydroxyaryl group, a $C_4$-$C_{20}$ alkylheteroaryl group with 1 to 4 heteroatoms;
or a $C_1$-$C_4$ alkylcarboxylic moiety, which may be an acid, an amide, or which may be esterified with a $C_1$-$C_6$ alkyl group or a $C_7$-$C_{20}$ alkylaryl group;
$R^3$ represents a $C_1$-$C_4$ alkyl group;
$R^4$ represents a hydrogen atom, or a $C_1$-$C_4$ alkyl group;
$R^5$ represents a $C_1$-$C_4$ alkyl group; and
X represents an alkali metal.

An alkyl group is a linear, branched, or cyclic hydrocarbon chain. It may also be a combination of linear, branched, and cyclic structures. A $C_n$-$C_m$ alkyl is a hydrocarbon having n to m carbon atoms.

An aryl group is an aromatic hydrocarbon. The aryl may be monocyclic or polycyclic. In the case of polycyclic aryls, the individual aromatic rings may be fused or may be connected by single carbon-carbon bonds. Examples for suitable aryl groups are phenyl, biphenyl, naphtyl, anthryl, or phenanthryl. A $C_n$-$C_m$ aryl is an aromatic hydrocarbon having n to m carbon atoms.

A heteroaryl group is an aromatic hydrocarbon that contains 1 to 4 heteroatoms, preferably 1 to 2 heteroatoms. The heteroatoms may be oxygen, sulfur, and/or nitrogen. The heteroaryl may be monocyclic or polycyclic. The heteroaryl group may be attached to the main molecule through any of its carbon or nitrogen atoms.

An alkylaryl group is an aryl group that is substituted with one or more alkyl groups. The alkylaryl group may be attached to the main molecule through any of its alkyl or aryl carbon atoms. A $C_n$-$C_m$ alkylaryl contains n to m carbon atoms.

An alkylheteroaryl group is a heteroaryl group that is substituted with one or more alkyl groups. The alkyl substituents may be attached to the heteroaryl through any of the aromatic carbon or nitrogen atoms. The alkylheteroaryl group may be attached to the main molecule through any of the alkyl carbon atoms and/or the heteroaryl carbon or nitrogen atoms.

A hydroxyalkyl group is an alkyl group that is substituted with one or more hydroxyl groups. A $C_1$-$C_4$ hydroxyalkyl group contains 1 to 4 carbon atoms.

A thioether group refers to two alkyl groups that linked by a thioether bond. A $C_1$-$C_4$ thioether group contains 1 to 4 carbon atoms in total. The thioether group may be attached to the main molecule through any of its carbon atoms.

An alkylhydroxyaryl group is an alkylaryl group, in which any of the aryl carbon atoms are substituted with a hydroxyl group. The alkylhydroxyaryl group may be attached to the main molecule through any of its alkyl or aryl carbon atoms. A $C_n$-$C_m$ alkylhydroxyaryl contains n to m carbon atoms.

A $C_1$-$C_4$ alkylcarboxylic moiety, which may be an acid, an amide, or which may be esterified with a $C_1$-$C_6$ alkyl group or a $C_7$-$C_{20}$ alkylaryl group. In case of an amide, the nitrogen of the amide functionality is substituted with two hydrogen atoms. The alkyl ester group is a linear, branched, or cyclic hydrocarbon chain. It may also be a combination of linear, branched, and cyclic structures. An alkylaryl group is an aryl group that is substituted with one or more alkyl groups. The alkylaryl group may be attached to the carboxylic fragment through any of its alkyl or aryl carbon atoms. A $C_1$-$C_4$ alkylcarboxy group contains 1 to 4 carbon atoms in total.

By using amino acids in the form of Dane salts according to formulae II and III, the present invention circumvents the need for N-benzyloxycarbonyl or N-(tert-butyloxycarbonyl) protected amino acids. Furthermore, the enamine moiety in formulae II and III is readily cleaved under acid conditions to deprotect the α-amino group. Therefore, no additional steps to remove the protection groups are required.

Dane salts according to formulae II and III are easily accessible through the base-catalyzed reaction of the corresponding β-keto carboxylic acid esters with amino acids. As a further advantage of the present invention, the synthesis of the Dane salts from β-keto carboxylic acid esters with amino acids can be performed in situ, as there is no need to isolate the Dane salts from this reaction mixture prior to step a).

Unless specified otherwise, the denotation of any E/Z isomer regarding the double bond linking the two carbon atoms carrying $R^3$ and $R^4$ of the Dane salts mentioned in the context of the present invention is to be interpreted as comprising all other E/Z isomers regarding this bond of this compound as well. In solution, usually an equilibrium of the E- and the Z-configured Dane salts is present.

Preferably $R^1$ and $R^2$ independently represent a hydrogen atom, a n-butyl group, a t-butyl group, a propyl group, a cyclopropyl group, an ethyl group, or one of the side chains of the amino acids alanine, valine, leucine, isoleucine, methionine, phenylalanine, tyrosine, tryptophan, serine, threonine, glutamine, asparagine, esters of glutamic acid, or esters of aspartic acid. Here, the expression "side chain" refers to the substituent group attached to the α-carbon atom of an α-amino acid. Esters of glutamic or aspartic acid are esterified with a $C_1$-$C_6$ alkyl or a $C_7$-$C_{20}$ alkylaryl group on the side chain carboxylic acid moiety. Preferably, esters of glutamic or aspartic acid are esterified with an ethyl group on the side chain carboxylic acid moiety. For the above-mentioned amino acids, the side chains are methyl, isopropyl, isobutyl, sec-butyl, 2-thiomethyl-ethyl, benzyl, 4-hydroxybenzyl, 3-methylindol, hydroxymethyl, 1-hydroxyethyl, carboxamidoethyl, carboxamidomethyl, alkoxycarbonylethyl, alkoxycarbonylmethyl, arylalkoxycarbonylethyl, or arylalkoxycarbonylmethyl. In a particularly preferred embodiment, $R^1$ and $R^2$ independently represent a $C_1$ to $C_4$ unsubstituted alkyl group. In another particularly preferred embodiment, $R^1$ and $R^2$ independently represent one of the side chains of the amino acids alanine, valine, leucine, isoleucine, or phenylalanine.

$R^1$ and $R^2$ can be identical or different. If $R^1$ and $R^2$ are identical, the Dane salts according to formulae II and III are identical, i.e. a single Dane salt is used to synthesize the diamido compound according to formula I. The resulting diamido compound is symmetrically substituted. If on the other hand $R^1$ and $R^2$ are different, the resulting diamido compound according to formula I is a mixture of differently substituted diamido compounds.

Preferably, $R^3$ represents methyl. $R^4$ preferably represents hydrogen. $R^5$ preferably represents methyl or ethyl. In a particularly preferred embodiment, $R^3$ represents methyl, $R^4$ represents hydrogen, and $R^5$ represents ethyl. In this case, the Dane salts according to formulae II and III can be synthesized by reaction of ethyl 3-oxobutanoate with the corresponding amino acid.

X preferably represents a sodium atom or a potassium atom. More preferably, X represents a potassium atom.

In particularly preferred embodiment of the present invention, the Dane salts according to formulae II and III are selected from the following list.

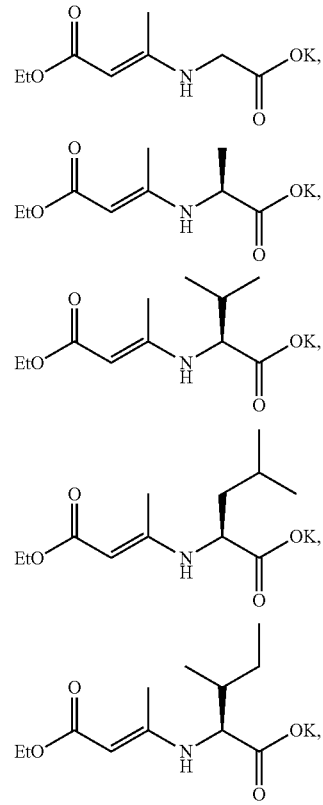

-continued

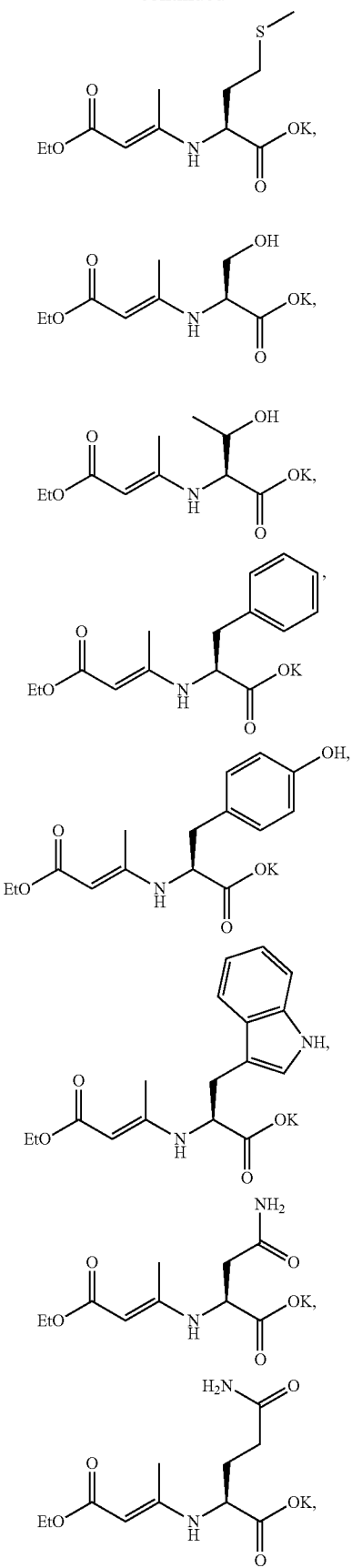

-continued

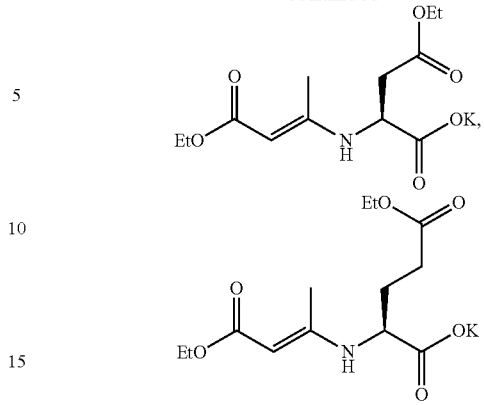

In step a) of the inventive method, the Dane salts according to formulae II and III are reacted with a coupling reagent to yield a Dane salt of an activated amino acid. The Dane salt of the activated amino acid is reactive towards amino groups and can be reacted with a diamino compound according to formula IV to couple the amino acid to the diamino compound by formation of an amide bond. Preferably, the amino acid is activated by formation of a mixed anhydride. Suitable coupling reagents for this purpose are, for example, pivaloylchloride, mesylchloride, biphenylphosphorylchloride or isobutylchloroformate. The coupling reagent can also represent a group of coupling reagents.

The reaction between the Dane salts according to formulae II and III and the coupling reagent is carried out in solution. The reaction temperature is adjusted according to the melting and the boiling point of the solvent and the thermal stability of the reagents. Preferably, the reaction is carried out at a temperature from −10 to +30° C., more preferably from 0 to 20° C.

Preferably the reaction between the Dane salts according to formulae II and III and the coupling reagent is carried out in a polar aprotic solvent. Suitable solvents for the present invention are, for example, dichloromethane, methyl tert-butyl ether, tetrahydrofuran, ethyl acetate, isopropyl acetate, dimethylformamide, acetonitrile, dimethylsulfoxide, methyl isobutyl ketone, methyl ethyl ketone, acetone or mixtures thereof.

Preferably, the Dane salts according to formulae II and III are first suspended in the solvent. Alternatively the Dane salts according to formulae II and III can also be synthesized in situ as described above. Then the coupling reagent is added, and the reaction mixture is stirred until the Dane salts have completely reacted with the coupling reagent. Preferably, the reaction time is up to 12 hours, more preferably 30 minutes to 2 hours.

Preferred diamino compounds according to formula IV are those, wherein L represents a $C_6$-$C_{12}$ linear alkyl group, a 1,4-dimethylcyclohexyl group, or a xylene group. In a particularly preferred embodiment, the diamino compound according to formula IV is selected from the following list.

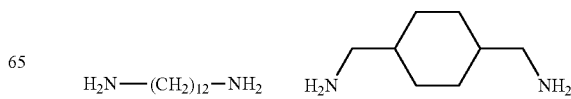

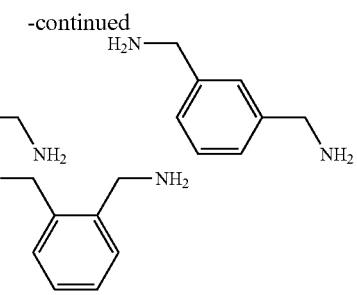

The reaction in step b) can take place at the same temperature as step a). Preferably, however, the temperature is adjusted to 10 to 30° C. after the diamino compound has been added to the reaction mixture of step a). After addition of the diamino compound the reaction mixtures is stirred until the reaction has reached completion. Preferably the reaction mixture is stirred up to 12 hours, more preferably 10 minutes to 1 hour.

Preferably the diamino compound is added along with a base, more preferably a non-nucleophilic base. Suitable compounds for this purpose are, for example, triethylamine, diisopropylethylamine, or mixtures thereof.

After step b) the reaction mixture is acidified by addition of an acid and water. Acidification results in hydrolysis of the enamine moiety and release of the diamido product according to formula I. Preferably the pH of the reaction mixture is adjusted to a value, which ensures complete hydrolysis of the enamine moiety, more preferably to a pH of 1 to 2. Preferably, the acid is an aqueous solution of hydrochloric acid.

The diamido product according to formula I can be further processed in situ or can be isolated from the reaction mixture after step c). Preferably, the diamido product according to formula I is isolated from the reaction mixture after step c). This can be achieved by extraction of the acidic, aqueous phase with a water immiscible, organic solvent and subsequently adjustment to a basic pH, preferably a pH above 10 and extraction of the diamido product by a water immiscible, organic solvent. The diamido product can be further purified by crystallization from the organic phase.

In preferred embodiment of the invention, the inventive method is carried using a polar aprotic solvent in steps a) and b), at a temperature of 0 to 20° C. during step a), at a temperature of 10 to 30° C. during step b), and at a pH of 1 to 2 in step c). In this embodiment, the Dane salt and the coupling agent form a mixed anhydride in step a) and the reaction between the product of step a) and the diamino compound according to formula III in step b) takes place in the presence of a non-nucleophilic base.

EXAMPLES

Example 1

Synthesis of N-(3-ethoxy-1-methyl-3-oxoprop-1-enyl)-L-valine potassium salt

L-Valine (117.2 g, 1.0 mol), KOH (85%, 66.0 g, 1 mol) and ethyl 3-oxobutanoate (140.2 mL, 1.1 mol) are dissolved in isopropyl acetate (1 L). The reaction mixture is heated to reflux using a Dean-Stark apparatus. 32 mL water are isolated during 1.75 h. A small quantity of precipitate is formed. 500 mL are distilled off.

The Dane-Salt solution is directly used for the next step.
Analytics of an Isolated Sample:
$^1$H-NMR (600 MHz, CDCl$_3$, major rotamer): δ=9.12 (d, J=6 Hz, 1H), 4.32 (s, 1H), 4.07-4.02 (m, 1H), 3.99-3.94 (m, 1H), 3.65-3.63 (m, 1H), 1.98-1.92 (m, 1H), 1.83 (s, 3H), 1.19 (t, J=12 Hz, 3H), 0.88 (d, J=6 Hz, 3H), 0.84 (d, J=6 Hz, 3H) ppm.

Example 2

Synthesis of N-(3-ethoxy-1-methyl-3-oxoprop-1-enyl)-L-phenylalanine potassium salt The Dane-Salt for L-phenylalanine is prepared as described for example 1.
Analytics of an Isolated Sample:
$^1$H-NMR (600 MHz, D$_2$O, major rotamer): δ=7.34-7.30 (m, 2H), 7.27-7.24 (m, 3H), 4.36 (s, 1H) 4.21-4.19 (m, 1H), 4.03-3.98 (m, 2H), 3.15 (dd, J=12 Hz, 6 Hz, 1H), 2.93 (dd, J=12 Hz, 6 Hz, 1H), 1.69 (s, 3H), 1.16 (t, J=12 Hz, 3H) ppm.

Example 3

Synthesis of

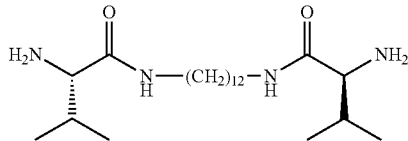

Isopropyl acetate (1.77 L) is added to the Dane-salt solution of example 1 and the mixture is cooled to 10° C. Pivaloyl-chloride (123.1 mL, 1 mol) is added. The temperature is rising to 17° C. The reaction mixture is stirred at 17° C. for 45 min and recooled to 10° C. In a separate flask, 1,12-diaminododecane (91.1 g, 0.46 mol) is dissolved in isopropyl acetate (1.57 L) and triethylamine (0.16 L, 1.14 mol) at 50° C. The solution is cooled to 10° C. The 1,12-diaminododecane solution is added in one portion to the Dane-salt solution. The temperature is rising to 20° C. The reaction mixture is stirred at room temperature for 30 min. Water (1.36 L) is added to the reaction mixture and the pH is adjusted to 1-2 by addition of conc. HCl (0.51 L). Isopropyl acetate is distilled off (approx. 3 L). The aqueous phase is separated and washed with isopropyl acetate (0.68 L). The organic phases are discarded. The aqueous phase is concentrated (approx. 1 L is distilled off) and treated with isopropyl acetate (1.0 L). The pH is adjusted to 10-11 by addition of NaOH (0.4 L) solution. The phase separation is performed at 70° C. The organic phase is separated and washed with water at 70° C. The solution is cooled to 0° C. and the precipitate is filtered off, washed with cold isopropyl acetate (2×0.2 L) and dried at 60° C. in vacuum. Yield: 121.4 g (67% over 2 steps).

$^1$H-NMR (600 MHz, DMSO): δ=7.75 (t, J=6 Hz, 2H), 3.10-2.99 (m, 4H), 2.88 (d, J=6 Hz, 2H), 1.85-1.80 (m, 2H), 1.58 (brs, 4H), 1.38 (t, J=6 Hz, 4H), 1.23 (s, 16H), 0.85 (d, J=6 Hz, 6H), 0.78 (d, J=6 Hz, 6H) ppm.

Example 4

Synthesis of

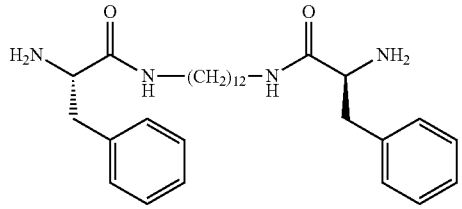

The same procedure as in example 3 is used except that the Dane salt solution from example 2 is used as a starting reagent.

$^1$H-NMR (600 MHz, DMSO): δ=8.51 (t, J=6 Hz, 2H), 8.40 (brs, 4H), 7.32-7.24 (m, 10H), 4.00-3.97 (m, 2H), 3.12-3.01 (m, 6H), 2.93-2.87 (m, 2H), 1.36-1.17 (m, 20H) ppm.

Example 5

Synthesis of

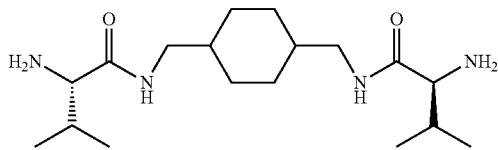 [SMILES: CC(C)[C@H](N)C(=O)NCC1CCC(CNC(=O)[C@@H](N)C(C)C)CC1]

The same procedure as in example 3 is used except that 1,4-Cyclohexanedimethaneamine is used as diamine.

$^1$H-NMR (600 MHz, DMSO): δ=7.65 (t, J=6 Hz, 2H), 3.21-3.11 (m, 4H), 2.77 (d, J=6 Hz, 2H), 2.10-2.04 (m, 2H) 1.95-1.90 (m, 2H), 1.62 (brs, 4H), 1.51-1.42 (m, 4H), 1.23-1.16 (m, 4H) 0.89 (d, J=6 Hz, 6H), 0.79 (d, J=6 Hz, 6H) ppm.

The invention claimed is:

1. Method for the synthesis of a compound according to formula I

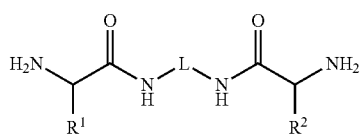

(I)

comprising the following steps:
a) reacting a Dane salt according to formula II

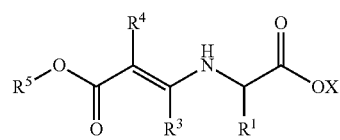

(II)

and a Dane salt according to formula III

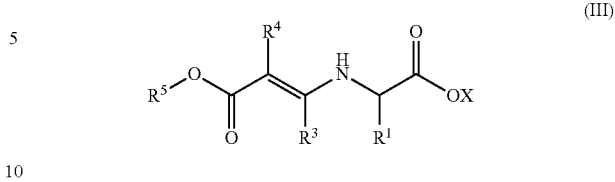

(III)

with a coupling reagent;
b) adding a diamine according to formula IV

(IV)

to the reaction mixture; and
c) adding an acid to the reaction mixture to adjust the pH value of the reaction to <7; wherein
L represents a $C_2$-$C_{20}$ alkyl group, a $C_6$-$C_{20}$ aryl group, or a $C_7$-$C_{20}$ alkylaryl group;
$R^1$ and $R^2$ can be identical or different and represent a hydrogen atom, a $C_1$-$C_4$ alkyl group, a $C_1$-$C_4$ hydroxyalkyl group, a $C_1$-$C_4$ thioether group, a $C_6$-$C_{20}$ aryl group, a $C_7$-$C_{20}$ alkylaryl group, a $C_7$-$C_{20}$ alkylhydroxyaryl group, a $C_4$-$C_{20}$ alkylheteroaryl group with 1 to 4 heteroatoms;
or a $C_1$-$C_4$ alkylcarboxylic moiety, which may be an acid, an amide, or which may be esterified with a $C_1$-$C_6$ alkyl group or a $C_7$-$C_{20}$ alkylaryl group;
$R^3$ represents a $C_1$-$C_4$ alkyl group;
$R^4$ represents a hydrogen atom, or a $C_1$-$C_4$ alkyl group;
$R^5$ represents a $C_1$-$C_4$ alkyl group; and
X represents an alkali metal.

2. Method according to claim 1, wherein $R^1$ and $R^2$ can be identical or different and represent a hydrogen atom, a n-butyl group, a t-butyl group, a propyl group, a cyclopropyl group, an ethyl group, or one of the side chains of the amino acids alanine, valine, leucine, isoleucine, methionine, phenylalanine, tyrosine, tryptophan, serine, threonine, glutamine, asparagine, esters of glutamic acid, or esters of aspartic acid.

3. Method according to claim 1, wherein L represents a $C_6$-$C_{12}$ linear alkyl group, a 1,4-dimethylcyclohexyl group, or a xylene group.

4. Method according to claim 1, wherein $R^3$ represents a methyl group.

5. Method according to claim 1, wherein $R^4$ represents a hydrogen atom.

6. Method according to claim 1, wherein $R^5$ represents a methyl or ethyl group.

7. Method according to claim 1, wherein X is Na or K.

8. Method according to claim 1, wherein $R^3$ and $R^4$ in formulae II and III have a cis configuration with respect to each other.

9. Method according to claim 1, wherein the coupling reagent is selected from the group consisting of pivaloylchloride, mesylchloride, biphenylphosphorylchloride or isobutylchloroformate or a mixture thereof.

10. Method according to claim 1, wherein in step c) the pH value is adjusted to pH 1-2.

11. Method according to claim 1, wherein the reaction in step a) is carried out at a temperature of −10 to +30° C.

12. Method according to claim 1, wherein the reaction in steps a) and b) is carried out in a polar aprotic solvent.

13. Method according to claim 12, wherein the solvent is selected from the group consisting of dichloromethane, methyl tert-butyl ether, tetrahydrofuran, ethyl acetate, isopropyl acetate, dimethylformamide, acetonitrile, dimethylsulfoxide, methyl isobutyl ketone, methyl ethyl ketone, acetone or mixtures thereof.

14. Method according to claim 2, wherein L represents a $C_6$-$C_{12}$ linear alkyl group, a 1,4-dimethylcyclohexyl group, or a xylene group.

15. Method according to claim 2, wherein $R^3$ represents a methyl group.

16. Method according to claim 3, wherein $R^3$ represents a methyl group.

17. Method according to claim 2, wherein $R^4$ represents a hydrogen atom.

18. Method according to claim 3, wherein $R^4$ represents a hydrogen atom.

19. Method according to claim 4, wherein $R^4$ represents a hydrogen atom.

20. Method according to claim 2, wherein $R^5$ represents a methyl or ethyl group.

* * * * *

UNITED STATES PATENT AND TRADEMARK OFFICE
CERTIFICATE OF CORRECTION

| | | |
|---|---|---|
| PATENT NO. | : 9,126,896 B2 | Page 1 of 1 |
| APPLICATION NO. | : 14/386540 | |
| DATED | : September 8, 2015 | |
| INVENTOR(S) | : Martin Bindl, Roland Herrmann and Gunter Knaup | |

It is certified that error appears in the above-identified patent and that said Letters Patent is hereby corrected as shown below:

Claims

Under column 10 of the patent at line 5, claim 1, the formula should be corrected as shown below.

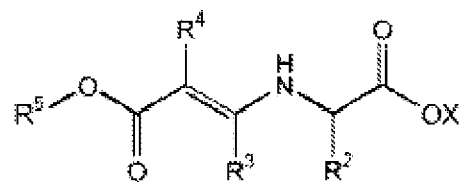

Signed and Sealed this
Second Day of February, 2016

Michelle K. Lee
*Director of the United States Patent and Trademark Office*